(12) United States Patent
DiFoggio

(10) Patent No.: US 7,530,265 B2
(45) Date of Patent: May 12, 2009

(54) METHOD AND APPARATUS FOR ELEMENTAL ANALYSIS OF A FLUID DOWNHOLE

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 195 days.

(21) Appl. No.: 11/235,570

(22) Filed: Sep. 26, 2005

(65) Prior Publication Data

US 2007/0068242 A1 Mar. 29, 2007

(51) Int. Cl.
*E21B 49/08* (2006.01)
(52) U.S. Cl. .................................. 73/152.42
(58) Field of Classification Search ............... 73/152.42
See application file for complete search history.

(56) References Cited

U.S. PATENT DOCUMENTS

| | | | |
|---|---|---|---|
| 4,561,777 A | 12/1985 | Radziemski et al. | |
| 4,986,658 A | 1/1991 | Kim | |
| 4,992,834 A | 2/1991 | Yamamoto et al. | |
| 4,995,723 A | 2/1991 | Carlhoff et al. | |
| 5,091,652 A | 2/1992 | Mathies et al. | |
| 5,256,852 A | 10/1993 | Boudot | |
| 5,379,103 A * | 1/1995 | Zigler | 356/73 |
| 5,446,538 A | 8/1995 | Noll | |
| 5,469,255 A | 11/1995 | Kamada et al. | |
| 5,608,519 A | 3/1997 | Gourley et al. | |
| 5,751,416 A | 5/1998 | Singh et al. | |
| 5,859,430 A * | 1/1999 | Mullins et al. | 250/255 |
| 6,034,768 A * | 3/2000 | Fraser et al. | 356/316 |
| 2001/0036667 A1 * | 11/2001 | Tayebi et al. | 436/56 |
| 2006/0241867 A1 * | 10/2006 | Kuchuk et al. | 702/13 |

OTHER PUBLICATIONS

Z. A. Arp et al.; Preliminary Study of Laser-Induced Breakdown Spectroscopy (LIBS) for a Venus Mission, Lunar and Planetary Science XXXV (2004), pp. 1-11.

P. Rambo et al.; High-voltage electrical discharges induced by an ultrashort-pulse UV laser system. J. Opt. A: Pure Appl. Opt. 3, 2001, pp. 146-158.

ESTCP Cost and Performance Report, (CU-9716), Site Characterization and Analysis Penetrometer System (SCAPS) Heavy Metal Sensors, Apr. 2003, Table of Contents 1-vi, pp. 1-34.

(Continued)

*Primary Examiner*—Hezron E. Williams
*Assistant Examiner*—Paul M West
(74) *Attorney, Agent, or Firm*—Madan, Mossman & Sriram PC

(57) ABSTRACT

The present invention provides a method and apparatus for performing elemental analysis of a formation fluid downhole. The present invention provides elemental analysis of a formation fluid downhole using breakdown spectroscopy. In one aspect of the invention, a method and apparatus are provided for performing laser induced breakdown on a formation fluid sample is provided. In another aspect of the invention a method and apparatus are provided for performing spark induced breakdown spectroscopy. Plasma is induced in a fluid under test downhole. Emissions from the plasma are analyzed to determine the elemental composition of the fluid under test. Emissions include but are not limited to light in the ultraviolet, visible, and near infrared regions of the spectrum. A spectrometer is provided for elemental analysis of a fluid downhole. Elemental analysis yields information about the fluid and the formation from which the fluid originated.

24 Claims, 4 Drawing Sheets

OTHER PUBLICATIONS

K. M. Lo et al.; ArF Laser-Induced Plasma Spectroscopy for Part-per-Billion Analysis of Metal Ions in Aqueous Solutions, Applied Spectroscopy, vol. 56, No. 6, 2002, pp. 682-688.

Laser-Induced Breakdown Spectroscopy, http://www.appliedphotonics.force9.co.uk/About_LIBS/about_libs.html.

* cited by examiner

METHOD AND APPARATUS FOR ELEMENTAL ANALYSIS OF A FLUID DOWNHOLE

BACKGROUND OF THE INVENTION

1. Field of the Invention

The present invention relates to compositional analysis of a fluid sample downhole. More particularly, the present invention relates to the elemental analysis of samples downhole such that they may be analyzed for their constituent components via laser induced breakdown spectroscopy (LIBS), spark-induced breakdown spectroscopy (SIBS) or some similar technique of plasma generation and optical emission analysis.

2. Summary of Related Art

There are many situations where it is necessary or desirable to obtain substantially instantaneous and/or immediate major and trace constituent analysis of a sample material. Sample materials may include geological samples, soil samples, powder metallurgy, ceramics, food, pharmaceuticals, and many other materials. There are many reasons why it would be desirable to test these materials for their composition of components. Hydrocarbon production is costly and knowing that production of a particular hydrocarbon bearing formation is not feasible due to content of undesirable elements such as sulfur may deem a formation infeasible. Compartmentalization is also a problem encounter during hydrocarbon production and the existence of such compartmentalization is valuable knowledge affecting production decisions involving millions of dollars in production expense.

There is currently no known method and apparatus for performing elemental analysis downhole. It would be useful to perform elemental analysis downhole on formation fluid to determine the characteristics of a formation fluid sample and the formation from which the fluid originated.

SUMMARY OF THE INVENTION

The present invention provides a method and apparatus for performing elemental analysis of a formation fluid downhole. The present invention provides elemental analysis of a formation fluid downhole using breakdown spectroscopy. Plasma is induced in a fluid under test downhole. Emissions from the plasma are analyzed to determine the composition of the fluid under test. Emissions include but are not limited to light in the ultraviolet, visible, and near infrared regions of the spectrum. A spectrometer is provided for elemental and compositional analysis of a fluid downhole. Compositional analysis yields information about the fluid and the formation from which the fluid originated. In one aspect of the invention, a method and apparatus for performing laser induced breakdown on a formation fluid sample is provided. In another aspect of the invention a method and apparatus are provide for performing spark induced breakdown spectroscopy. It is well known how to apply breakdown spectroscopy in air in the laboratory at room pressure. However, applying this technology downhole presents several challenges. First of all, downhole fluids are typically under tremendous pressures of 10-20 kpsi. Therefore, to apply such a technique downhole, sufficient energy must be applied over a small enough volume within a short enough period of time (for example by using a strong enough laser or a spark), so as to raise the temperature high enough (about 10,000 C) that the pressure within the plasma exceeds the pressure within the fluid. In this way, it becomes possible for a small bubble of plasma to form within the high pressure fluid. Secondly, it must be possible to detect the light coming from this bubble of plasma even though this bubble is immersed within a dark fluid (such as crude oil) that strongly absorbs the light which it emits.

BRIEF DESCRIPTION OF THE DRAWINGS

Objects and advantages of the invention will become apparent upon reading the following detailed description and upon reference to the accompanying drawings in which.

DETAILED DESCRIPTION OF THE INVENTION

Figure 1:
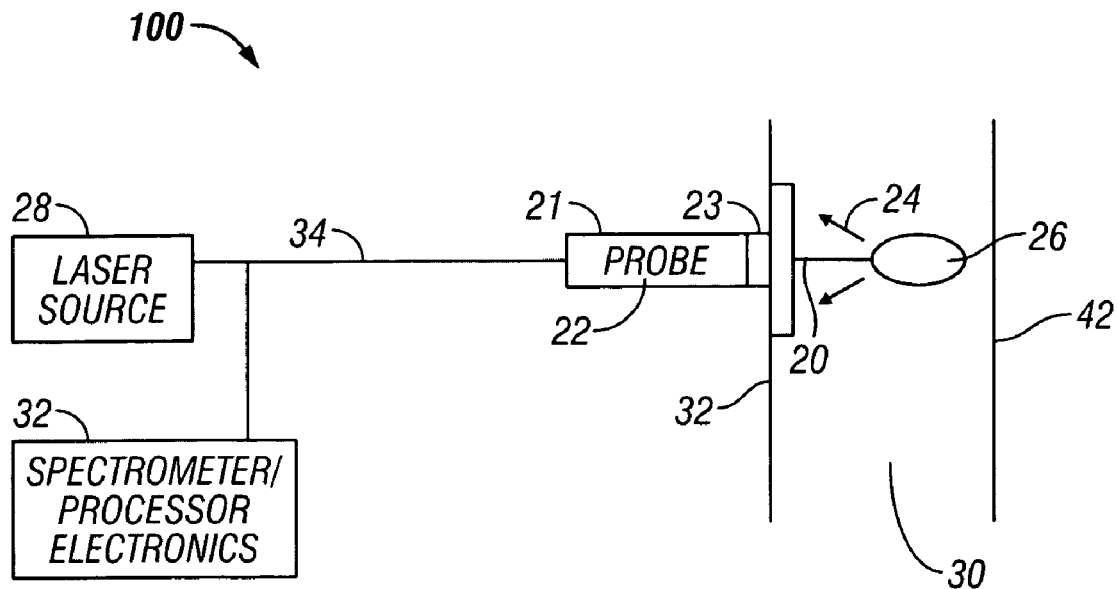
FIG. 1 is an illustration of an exemplary embodiment of the present invention showing a laser induced breakdown spectroscopy apparatus interacting with a fluid through a window.

The present invention is susceptible to embodiments of different forms. There are shown in the drawings, and herein will be described in detail, specific embodiments of the present invention. This exemplary disclosure is provided with the understanding that it is to be considered an exemplification of the principles of the invention, and is not intended to limit the invention to that illustrated and described herein. In particular, various embodiments of the present invention provide a number of different constructions and methods of operation, and modifications thereof can be made by one skilled in the art without departing from the spirit and teachings of the invention. It is to be fully recognized that the different teachings of the embodiments discussed below may be employed separately or in any suitable combination to produce desired results.

The present invention provides a method and apparatus for generating a plasma by using a spark or by applying a laser beam to a target sample and performing laser induced breakdown spectroscopy (LIBS), or laser-induced plasma spectroscopy (LIPS), for downhole, in situ, primary composition and impurity analysis. The present invention provides a method for collecting the light from a bubble of plasma either by generating the bubble at the interface between a downhole fluid and an optical window or by generating the bubble at the tip of an optical fiber. The sensitivity of breakdown spectroscopy varies by element. One can expect a minimum detectable sensitivity of less than a 1 ppm for Be, Mg, Cr, Fe, Ag, Hg; of 1-10 ppm for Li, B, Na, Cl, Ca, Ti, Mn, Ni, Cu, Zn, Sr, Ba, Pb, Th; of 10-100 ppm for C, F, Al, Si, S, K, Co, Ga, Rb, Zr, Nb, Tc, Pd, Cd, Sn, Cs, Eu, Pt, Tl; of 100-500 ppm: P, V, Ge, As, Mo, I, Au, Bi; and of more than 500 ppm for Y, In, Sb, Te, Hf, W. Breakdown spectroscopy tends to be only qualitative for H, N, O, Ar, Sc, Ru, Rh, Gd, Er, Re, U, Pu, and Am.

Figure 2:
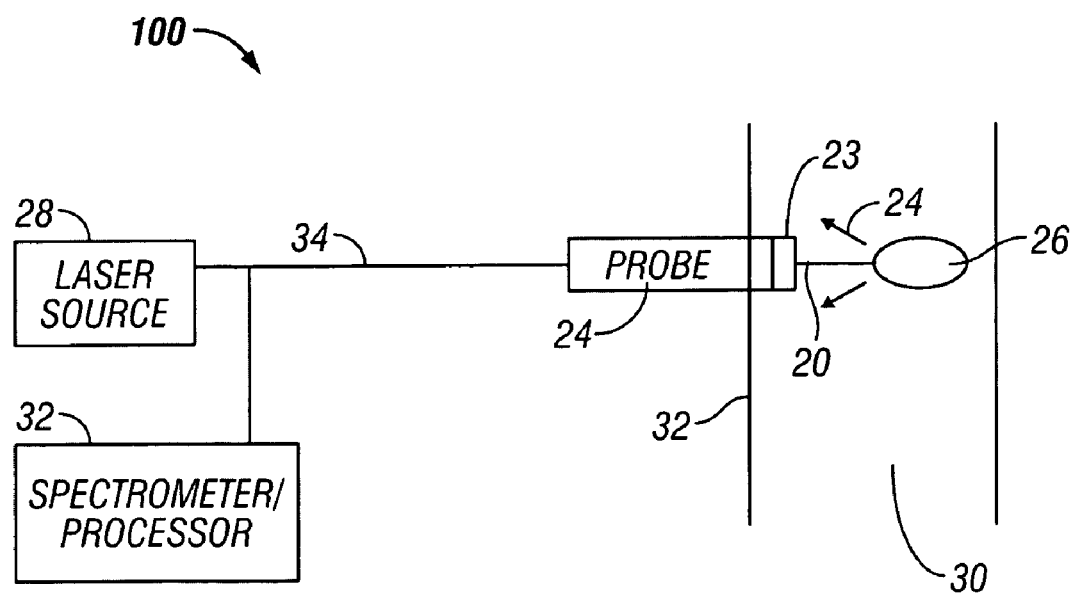
FIG. 2 is an illustration of is an illustration of an exemplary embodiment of the present invention showing a laser induced breakdown spectroscopy apparatus inserted into and interacting with a fluid.

LIBS is a useful method for determining the elemental composition of various solids, liquids, and gases. Referring now to FIG. 1, in an exemplary embodiment of the present invention 100, using the LIBS technique, a high power laser pulse 20 is focused on to a sample 30 to create a plasma or laser spark at a test point or focal region. The spark in the focal region generates a high density plasma plume 26 which produces and excites various atomic elements. Atomic emission 24 from the plasma may be collected with a collimating lens or fiber optics, and analyzed by a spectrograph and gated detector. The atomic spectral lines can be used to determine the elemental composition or the elemental concentrations in the sample. The analysis is similar to that performed by an inductively-coupled plasma (ICP) analyzer, known to those skilled in the art. A laser source 28 provides the laser pulse to probe 22 and spectrometer/processor electronics 32 process and analyze the collected emissions from the plasma. Probe 22 may interact with the fluid 30 inside of fluid conduit 42 through window 32 or the probe 22 may be inserted into the fluid 30 as shown in a FIG. 2. The laser pulse is delivered to the probe 22 via an optical conduit 34, such as for example, a fiber optic cable. The optical conduit 34 also collects light emitted from the plasma 26 and delivers the collected light to spectrometer processor electronics 32. Preconditioning and gating occurs in electronics 32.

LIBS can be applied using a variety of lasers, but typically excimers or pulsed Nd:Yag lasers are used. Gas tube lasers or diode lasers could also be used. The high intensity laser pulse 20 interacting with sample 30 produces a plasma plume 26 that evolves with time from the point of impact 22 of the incident laser pulse. The laser pulse usually lasts for less than 20 nanoseconds (ns). Emissions 24 from plasma plume 26 are collected and analyzed by the detection system. Typically emission 24 is collected at some distance from sample 30 to reduce the effect on the data from self-absorption effects or surface effects. Ideally, the plasma created breaks down all the sample's chemical bonds and ionizes many of the constituent elements. The spectral emission occurs as a result of the subsequent relaxation of the constituent excited species.

For a more detailed explanation of LIBS devices and technology, reference is made to U.S. Pat. No. 5,751,416 to Singh et al., entitled Analytical Method using Laser Induced Breakdown Spectroscopy, which is incorporated herein by reference as though fully set forth in its entirety.

The present invention is useful for analysis of formation fluid extracted from a dilled wellbore or for analysis for fluid in a monitoring while drilling operation when deployed from a drill string or coiled tubing. The term fluid is used in this specification to mean a gas, fluid or a multiphase mixture of gas, fluid and condensate or particulate suspended therein. In an alternative embodiment, the present invention may also be deployed in a pipeline for analysis of fluid transported in the pipeline. In each case, a LIBS device is provided to perform elemental analysis of a fluid associated with the deployment environment. Similarly, a spark induced spark spectroscopy (SIBS) device may be used in place of the LIBS device for elemental analysis of the fluid. Elemental analysis enables the present invention to estimate the composition of a fluid and estimate a property of the formation from which the fluid originated.

Spark induced breakdown spectroscopy (SIBS), Laser-Induced Plasma Spectroscopy (LIPS) or, as it is more often known, Laser-Induced Breakdown Spectroscopy (LIBS), is a form of atomic emission spectroscopy in which a pulsed laser is used as the excitation source. The output of a pulsed laser, such as a Q-switched Nd: YAG, is focused into or onto the surface of or of the material to be analyzed. For the duration of the laser pulse, which is typically 10-20 nanoseconds, the power density at the surface of the material can exceed 1 Giga watt per $cm^2$ using only a compact laser device and simple focusing lenses.

At these very high power densities, a fraction of a microgram of material is ejected from the surface by a process known as laser ablation and a short-lived but highly luminous plasma with instantaneous temperatures reaching 10,000° C. is formed at the surface of the material. Within this hot plasma, the ejected material is dissociated into excited ionic and atomic species. At the end of the laser pulse, the plasma quickly cools as it expands outwards at supersonic speeds. During this time the excited ions and atoms emit characteristic optical radiation as they revert to lower energy states. Detection and spectral analysis of this optical radiation using a sensitive spectrograph can be used to yield information on the elemental composition of the material.

Time-gated detectors are employed in electronics 32 which allow the optical emission from the laser plasma to be recorded at some time delay after the laser pulse. This is desirable since the characteristic atomic and ionic emission lines only start to appear after the plasma has expanded and cooled.

The plasma plume emission is collected by the fiber optics and analyzed by the detection system, comprising a spectrometer. The chemical bonds of the sample are broken by the created hot plasma and it ionizes the constituent elements. After the relation of the constituent excited species, spectral emission occurs. The timing of the spectral emission lines vary with the type of sample, but also with distance from the center of the plasma. The wavelength of the incident laser light is also a factor. The evolution of the plasma and the changes in its content occur on microsecond timescales. The LIBS apparatus can also be used for laser-induced fluorescence spectroscopy (LIF).

In LIBS, a small volume of the target fluid is intensely heated by the focused beam of a pulsed laser and thus brought to a transient plasma state where the sample's components are essentially reduced to individual atoms. In the high temperature plasma, atoms are ionized, or brought to excited states. Such state decay is characterized by emission of radiation, which is observed in the ultraviolet (UV), visible and near-infra red (NIR) region of the electromagnetic spectrum. Spectrometric processing of the UV, visible and NIR light emissions enables compositional and elemental analysis of a fluid under test downhole.

The LIBS device comprises a laser to provide a short pulse of for example, 20 nanoseconds (ns) or less duration. Because this time is so short, only a small of energy need be applied, for example 10 micro joules (mj) per pulse to achieve very high power levels (energy per unit time). Optics are provided in the present example through a fiber optic cable. The fiber optic cable (which can be metal coated over most of its length for spark induced breakdown spectroscopy) acts as a LIBS laser source having an open end for delivering the laser pulse to a fluid under investigation. Optics are also provided to capture light emitted from the fluid under investigation in the area of incidence for the laser beam. A spectrometer is also provided detect and separate the light from different elements and ions for chemical identification for elemental analysis of the fluid under investigation. Upon striking the fluid sample, a plasma is formed from which emitted light generates traces from the elements contained in the fluid.

The LIBS laser source and LIBS light collector are combined into a single optical fiber in the present example, but may be separated into separate optical fibers. Either or both of the LIBS laser source optical fiber and the LIBS light collection optical fiber may be inserted into a fluid under investigation or may send or collect light into and from the fluid through a window that allows the passage of emitted and/or collected light.

The LIBS apparatus is sensitive to substantially all elements in varying degree with a typical limit of detection on the order of 0.1 to 200 parts per million depending on the sample and the element of interest. The present invention enables a number of complex analyses including but not limited to determination of composition, origin of fluids during drilling operations, fluid production and fluid distribution.

As shown in FIG. 1, the LIBS laser light source 28 comprises an optical fiber 34 that conveys the laser pulse 20 to a particular location in the fluid 30 under investigation and collects light 24 from the plasma formed in the fluid upon application of the laser light pulse to the fluid. A plasma 26 is induced or created by the high intensity laser pulse. For spark-induced breakdown spectroscopy (SIBS), the optical fiber may be coated with metallic coating 21 over most of the fiber to make most of its length electrically conducting excluding the tip 23. Furthermore, the tip 23 of the fiber can be also coated with an optically-transparent but electrically-conductive coating (such a tin oxide or indium tin oxide). A spark occurs in a fluid wherever the electric field exceeds the breakdown field strength of that fluid. To facilitate spark creation, for any given voltage, one can increase the local electric field strength by decreasing the radius of curvature of the electrode. The electric field around a conductor increases inversely with the radius of curvature of that conductor. Therefore, one can enhance spark creation for a given voltage by creating a spark between a fiber optic cable whose tip may be sharpened to a point and covered with an optically-transparent but electrically-conductive coating 25 and either a metal plate or a metal needle. The end of the fiber 23 is light transmissive to allow the laser light pulse to enter the fluid 30. Plasma 26 is induced in the fluid by the high intensity laser pulse 20. The optical probe end 23 then collects light emitted from the plasma and passes through the optical conduit 34 the spectrometer/processor electronics 32 analysis system.

Figure 3:
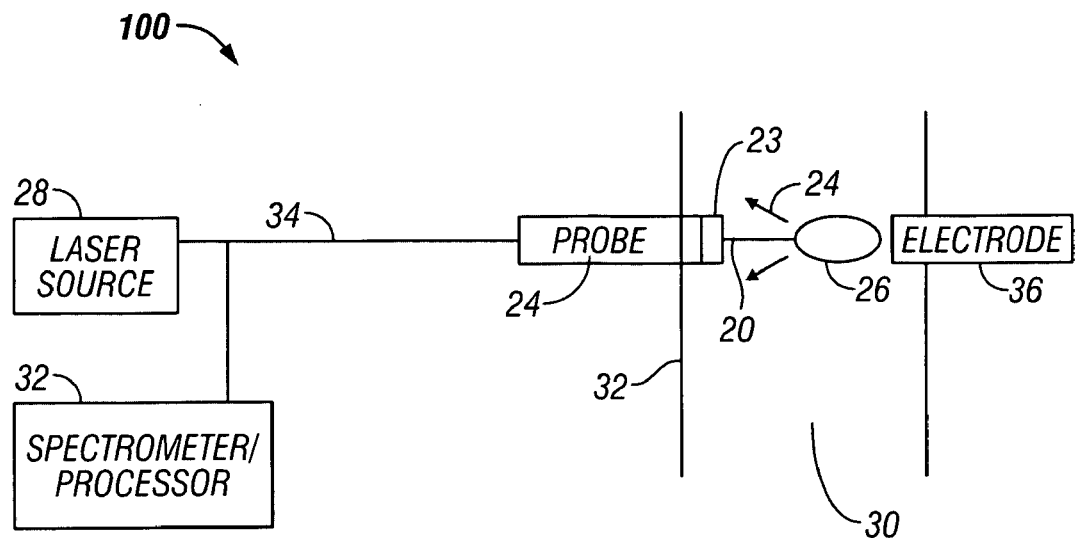
FIG. 3 is an illustration of is an illustration of an exemplary embodiment of the present invention showing a spark induced breakdown spectroscopy apparatus inserted into and interacting with a fluid.
Figure 7:
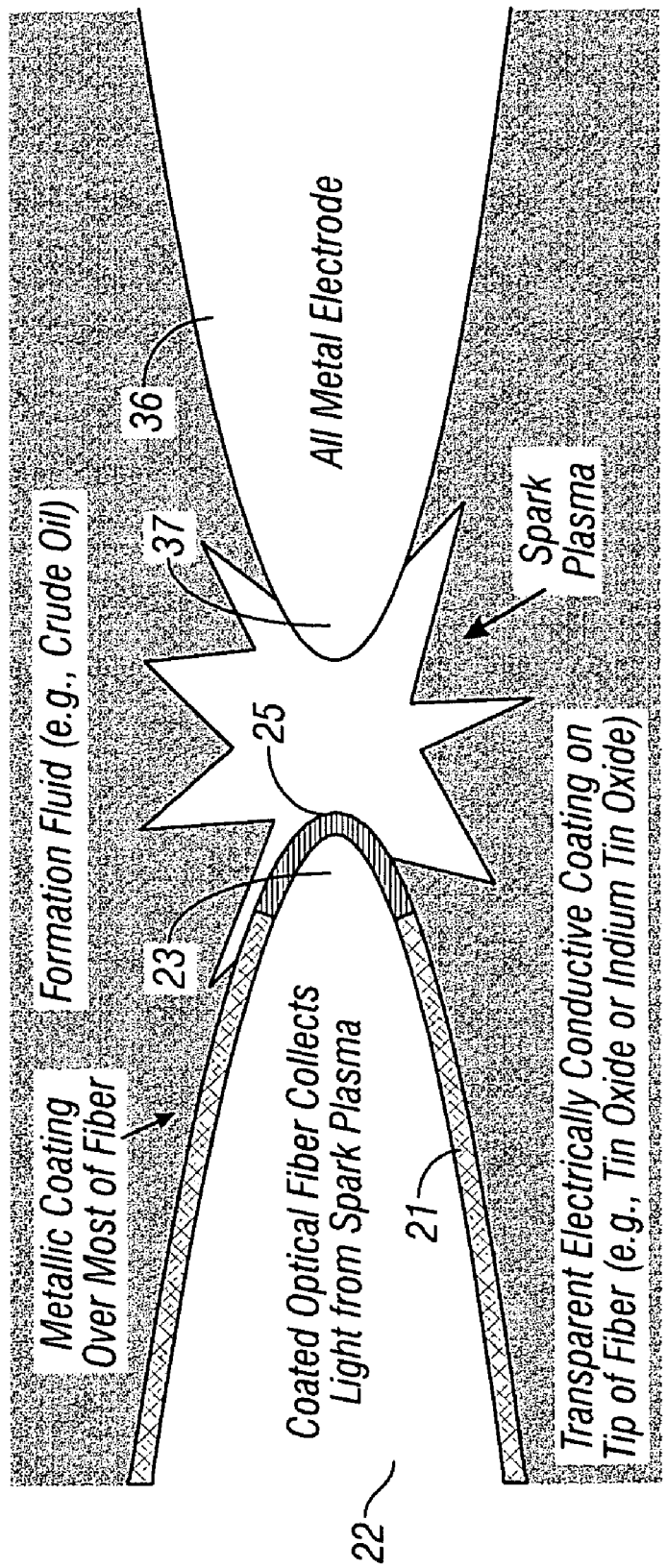
FIG. 7 is a more detailed schematic representation of the spark induced breakdown spectroscopy apparatus.

In an alternative embodiment as shown in FIG. 3, an electrode 36 induces a spark into the fluid 30. The spark generates or induces plasma 26 in the fluid. The optical probe end 23 collects light 24 emitted from the plasma formed in the fluid and passes the collected light through the optical conduit 34 the spectrometer/processor electronics 32 analysis system. A plasma is created by the high intensity laser pulse. The optical fiber is coated with metal over most of the fiber and can have an electrically conducting but optically transparent coating (such as tin oxide or indium tin oxide) over its tip. The end of the optical conduit or fiber 23 is light transmissive to collect light from the spark induced plasma and deliver the collected light to a spectrometer for analysis. Plasma is created in the fluid by the high intensity laser pulse. A more detailed schematic representation of the electrode 36 is shown in FIG. 7. As shown in FIG. 7, the probe 22 may have a pointed tip 23 coated with optically transmissive material 25. The portion of the probe 22 excluding the tip may be substantially coated with metallic coating 21. As shown in FIG. 7, the electrode may have a shaped or pointed end 37 to enhance an electric field generated by the electrode into the formation fluid for generating a spark.

The elemental analysis is useful to determine the origin of fluids in exploration, production, drilling and delivery operations. In exploration, one would like to know which zones of hydrocarbons are the most economic to produce. Hydrocarbons containing a high level of sulfur require additional processing to remove the sulfur so they have less value. Similarly, additional processing is needed to remove mercury, which will become increasingly important as stricter environmental regulations go into effect regarding the allowed parts per billion concentrations of mercury in refined petroleum products. Also, hydrocarbons having high levels of nickel or vanadium have less value because these elements can ruin the expensive catalysts (which can exceed a million dollars or more per catalytic unit) that refineries use to process crude oil. Also, fluids from different wells or fluids from different depths in the same well can be compared to determine compartmentalization of the reservoir. In production, changes in elemental composition of a particular zone over time can indicate that drainage of the oil field has started to extent to a new region of the reservoir and therefore help us in understanding connectivity of the reservoir. Analyses can be performed on brines or on hydrocarbon fluids (liquids or gases). In drilling operations, compositional analysis can also be performed on fluid samples to determine the content of certain desirable and undesirable substances such as sulfur. It may be that a formation or compartmentalized layers penetrated by a well within a formation containing undesirable substances may not be produced. The contribution of injections wells to a formation can be determined by analyzing the composition of the fluid to determine if trace elements or tracers uniquely present in a particular injection well or wells is present in the fluid or a formation. An elemental tracer, not normally present downhole for which the technique has high sensitivity, can be used to determine reservoir connectivity.

Figure 4:
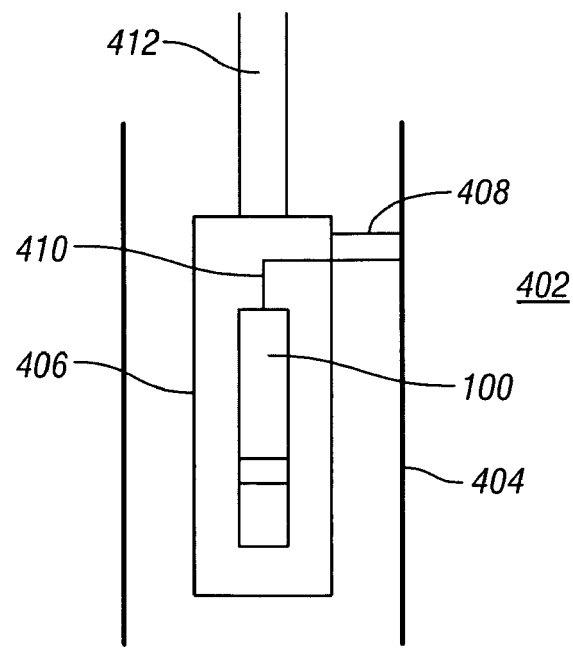
FIG. 4 is an illustration of is an illustration of an exemplary embodiment of the present invention shown deployed in a borehole via a conveying mechanism.

As shown in FIG. 4 the present invention 100 is deployed down hole in a wellbore 404 drilled into a formation. The present invention may be deployed via a conveyance device 412 comprising but not limited to a wireline, a drill string or coiled tubing or in a production or distribution pipe. Fluid is extracted from a formation 402 and passed through a flow line 410 into downhole tool 406. The present invention, contained in downhole tool 406 then analyzes the fluid using breakdown spectroscopy of emitted light from plasma induced in the fluid as discussed above. Thus, the present invention can be used to analyze fluid while drilling, after drilling, during production and during distribution of the fluid.

Figure 5:
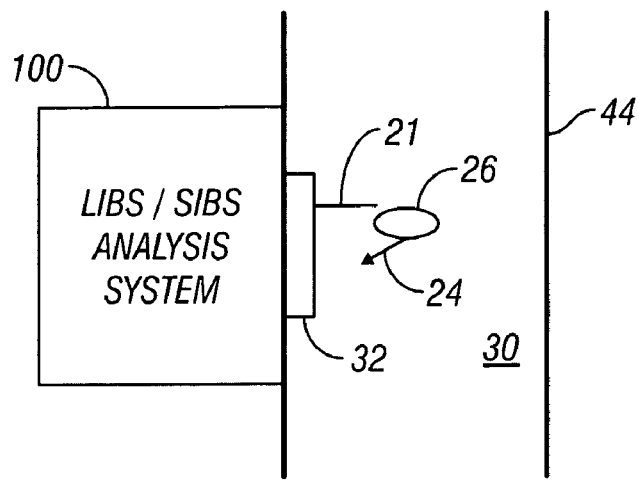
FIG. 5 is an illustration of an exemplary embodiment of the present invention shown deployed in association with a distribution conduit.

Turning now to FIG. 5, an alternative embodiment of the present invention is illustrated. As shown in FIG. 5 the present invention 100 can be deployed for elemental analysis of fluids 30 passing through a distribution conduit 44. Thus, the origin and quality of distributed fluids (petroleum and natural gas) can be assessed at their destination or during distribution in distribution conduit 44.

Figure 6:
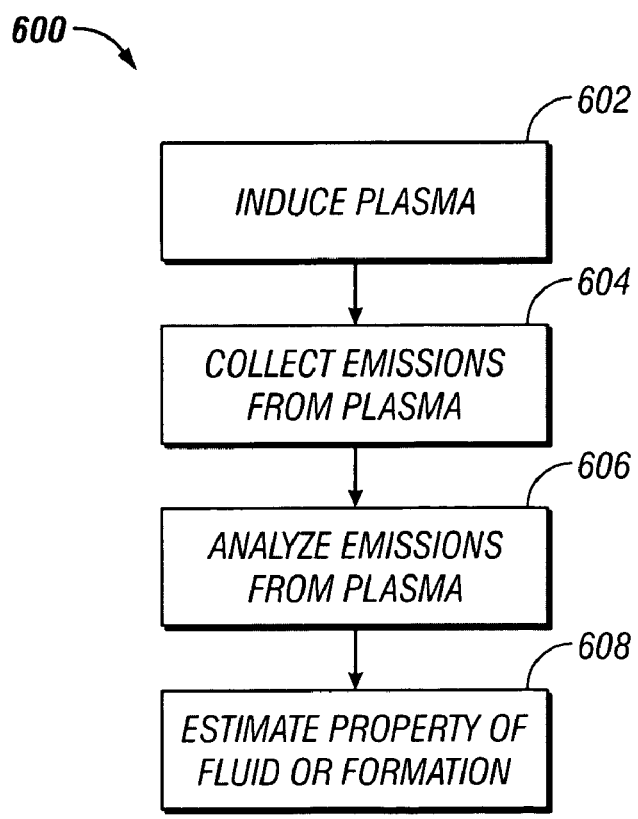
FIG. 6 is an illustration of functions and acts performed by an exemplary embodiment of the present invention.

Turning now to FIG. 6 a flow chart 600 of functions and acts performed in an exemplary embodiment of the invention is illustrated. The present invention induces plasma in a fluid under test 602 and collects emissions from the plasma 604. The emissions are passed to the processor/spectrometer/electronics for analysis to estimate composition and elemental analysis 606. The analysis enables the present invention to estimate a property of the fluid (composition, etc.) or a property the formation (compartmentalization, contribution of injection wells to a formation by tracing origin of fluids form injection wells in a fluid under investigation, etc.)

The present invention has been described as method and apparatus operating in a down hole environment in the preferred embodiment, however, the present invention may also be embodied as a set of instructions on a computer readable medium, comprising ROM, RAM, CD ROM, Flash or any other computer readable medium, now known or unknown that when executed cause a computer to implement the method of the present invention. While a preferred embodiment of the invention has been shown by the above invention, it is for purposes of example only and not intended to limit the scope of the invention, which is defined by the following claims.

What is claimed is:

1. A method for estimating composition of a fluid downhole, comprising:
    collecting a fluid under pressure from a formation by a downhole tool;
    inducing plasma in the fluid downhole using a fiber tip coated with a substantially optically-transparent and electrically-conductive material;
    collecting light emission from the plasma by an optical sensor; and
    analyzing signals from the optical sensor using a processor to estimate the composition of the fluid downhole.

2. The method of claim 1, wherein inducing the plasma further comprises generating a laser pulse in the fluid.

3. The method of claim 1, wherein inducing the plasma further comprises generating a spark in the fluid.

4. The method of claim 1, wherein collecting the light emission from the plasma further comprises receiving light in a fiber optic cable.

5. The method of claim 4, wherein inducing the plasma in the fluid further comprises generating an electric spark in the fluid.

6. The method of claim 1, wherein analyzing the collected light emission further comprises performing an elemental analysis of the collected light emission.

7. The method of claim 1, further comprising:
    estimating a characteristic of a formation associated with the fluid.

8. The method of claim 7, wherein the characteristic is compartmentalization.

9. The method of claim 1, further comprising:
    injecting a tracer in the fluid.

10. The method of claim 1, wherein inducing the plasma in the fluid further comprises sending energy through a window into the fluid.

11. The method of claim 1, wherein the light emission further comprises light that is one of visible light, near infrared light and ultraviolet light.

12. The method of claim 1, wherein estimating the composition includes estimating presence of at least one of: Be, Mg, Cr, Fe, Ag, Hg, Li, B, Na, Cl, Ca, Ti, Mn, Ni, Cu, Zn, Sr, Ba, Pb, Th, C, F, Al, Si, S, K, Co, Ga, Rb, Zr, Nb, Tc, Pd, Cd, Sn, Cs, Eu, Pt, Tl, P, V, Ge, As, Mo, I, Au, Bi, Y, In, Sb, Te, Hf, W, H, N, O Ar, Sc, Ru, Rh, GD, Er Re, U, Pu and Am.

13. The method of claim 1, wherein analyzing the light emission is done by a spectrometer downhole.

14. An apparatus for estimating composition of a fluid downhole comprising:
    a chamber configured to receive a fluid under pressure from a formation;
    a plasma generator in communication with the fluid downhole configured to generate plasma in the fluid downhole using a fiber tip coated with a substantially optically-transparent and electrically-conductive material;
    an optical sensor in optical communication with the plasma generated in the fluid downhole; and
    a processor configured to process output from the optical sensor to estimate the composition of the fluid downhole.

15. The apparatus of claim 14, wherein the plasma generator further comprises an optical conduit configured to deliver a laser pulse to the fluid downhole.

16. The apparatus of claim 14, wherein the plasma generator further comprises an electrode configured to generate a spark in the fluid downhole.

17. The apparatus of claim 14, further comprising:
    a window between the plasma generator and the optical sensor.

18. The apparatus of claim 14, wherein the processor is further configured to perform elemental analysis of the light emission.

19. The apparatus of claim 18, wherein the processor is further configured to determine compartmentalization of a formation.

20. The apparatus of claim 18, wherein the processor is further configured to determine an origin of the fluid from the analysis.

21. The apparatus of claim 14, wherein the processor is further configured to estimate a characteristic of a formation associated with the fluid downhole.

22. An apparatus for estimating composition of a fluid downhole comprising:
    a plasma generator having a fiber tip coated with an optically-transparent and electrically-conductive coating configured to generate a spark in the fluid to generate a plasma in the fluid downhole;
    an optical sensor in optical communication with the plasma generated in the fluid downhole; and
    a processor configured to process output from the optical sensor to estimate the composition of the fluid downhole.

23. A downhole tool for estimating composition of a fluid downhole comprising:
    a pump configured to extract fluid from a formation;
    a chamber configured to hold the extracted fluid under pressure;
    a plasma generator configured to generate plasma in the fluid by a fiber tip coated with a substantially optically-transparent and electrically-conductive material;
    an optical sensor in optical communication with the plasma generated in the fluid downhole by the plasma generator; and
    a spectrometer including a processor configured to analyze output from the optical sensor to estimate the composition of the fluid downhole.

24. The downhole tool of claim 23, wherein the plasma generator comprises at least one of an optical conduit configured to deliver a laser pulse to the fluid downhole and an electrode configured to generate a spark in the fluid downhole.

* * * * *